United States Patent [19]

Silvestri

[11] 4,033,720

[45] July 5, 1977

[54] UNITARY SAMPLING AND ANALYSIS STRIP AND PROCESS

[75] Inventor: Achille Silvestri, Bel Air, Md.

[73] Assignee: The United States of America as represented by the Secretary of the Army, Washington, D.C.

[22] Filed: May 31, 1974

[21] Appl. No.: 475,079

[52] U.S. Cl. .................. 23/230 R; 23/253 TP
[51] Int. Cl.² ........................... G01N 31/22
[58] Field of Search ............ 23/230 R, 253 TP; 210/31 C, 198 C; 73/23.1, 61.1 C; 55/386

[56] References Cited

UNITED STATES PATENTS

| | | | |
|---|---|---|---|
| 3,552,928 | 1/1971 | Fetter | 23/253 TP |
| 3,628,915 | 12/1971 | Robertson | 23/230 R |
| 3,783,105 | 1/1974 | Moyer et al. | 23/253 TP |

OTHER PUBLICATIONS

Quantitative Thin Layer Chromatography, Touchstone, ed., Wiley and Sons, N. Y., pp. 305–309 (1973).
J. Chromatography, v. 37, pp. 508–517 (1968).
VWR Scientific Apparatus Catalog 72, p. 509 (1971).

Primary Examiner—Robert M. Reese
Attorney, Agent, or Firm—Nathan Edelberg; Robert W. Church; Robert P. Gibson

[57] ABSTRACT

A gas or liquid filter and analysis strip and process of detection using it with a thin-layer chromatographic process.

The invention described herein may be manufactured and used by or for the government for government purposes without the payment of royalties thereon or therefor.

1 Claim, 2 Drawing Figures

UNITARY SAMPLING AND ANALYSIS STRIP AND PROCESS

BACKGROUND OF THE INVENTION

In the sampling of fluid contaminants, numerous techniques are known. Of those used in the sampling of lethal and non-lethal contaminants, that disclosed and patented by Robertson in U.S. Pat. No. 3,628,915, has shown much promise and has been used by the common assignee. So also, his portable sampler has met with success, both under controlled and field conditions, and is presently being used.

The Robertson disclosed sampling apparatus and process, herein incorporated by references, is explained below. The apparatus comprises opposing hinged and apertured blocks between which is temporarily sandwiched filter collecting medium. One of the above mentioned apertures is closed by a suction pump hose. The other block aperture remains open for the atmosphere or sample medium. In operation, a differential pressure is created at the filter by actuating the suction pump and draining fluid from the sample medium through the filter. The contaminant is collected and left upon the filter ready to be analyzed. Analysis is had by the color comparison or the spot test technique. That is, the filter is impregnated with an analytical chemical material so that the collected chemical contaminant reacts therewith. The reaction causes a color change. Then to establish the presence of a contaminant, the color of the contaminant containing filter is compared with a color chart.

To detect incapacitating agents, I, along with others, have used a fluorescent test. It is based upon the fluorescent complex formed when an agent, such as a glycolate, combines with the indandione detector reagent. The incapacitants which are disseminated as microns-sized solid particles are sampled from the air or from surfaces using glass fiber filters. Sampling is accomplished by inserting a filter into Robertson's apparatus and operating it in the above described fashion. The sample is removed from the apparatus and sprayed with a reagent, the subject of another assignee invention filed in the U.S. Pat. Office on Aug. 7, 1969, entitled Detection of Glycolates and bearing Ser. No. 851,142, which is dispensed from an aerosol type can. The sprayed filter containing the sample is then viewed under ultra-violet light (366nm) through a Kodak N.9 Wratten photometric filter, manufactured by Eastman Kodak Company of Rochester, New York. This photometric filter isolates all visible radiation below 460nm. A yellow-orange fluorescence of the exposed portion of the filter constitutes a positive test.

Normally this test for incapacitating agents works well. However, if suspended debris, smokes from burning material, colored signalling smokes, and dusts are present, as would be the case in civil disruption or warfare, they too are collected. While these collected materials do not interfere with the reaction between the agent and reagent, their effect is to mask the fluorescence producted by the agent-reagent complex. This necessitates the use of some technique to separate these interferences from the agent to thereby enable the detection of the fluorescence and/or contaminant.

Separation of these masking materials, after trying diverse methods, is best achieved by thin-layer chromatography. This then requires that the sample must be removed from the filter and redeposited on an adsorbent medium used in thin-layer chromatography. As a result, samples are or have either been lost, contaminated further, or destroyed. Hence, the taking of a second and/or a third sample with tenant uncertain results has been common place. And all too often, after thin-layer chromatography steps detection with or without fluorescence is not reliable.

SUMMARY OF THE INVENTION

I have now discovered a manufacture and process without the above shortcomings. Reliability, consistency and accuracy in test environment with interferences for incapacitating agents is now had.

Briefly, my invention is a novel unitary support and filter and process of using it. The filter serves to collect the contaminants and the support serves as the adsorbent medium for the chromatographic process. Hence, my invention eliminates the deleterious sample transfer step.

OBJECTIVES

Therefore, it is an object of the present invention to provide a reliable system of detecting and testing for incapacitating agents;

Another object of the invention is to provide a new multipurpose filter and analysis strip and method of collecting and analyzing samples;

A further object of the invention is to provide a unitary contaminant filter for collecting samples and for acting as the separating medium in thin-layer chromatography.

These and other objects and advantages of the invention will become apparent from the following detailed description of the invention when considered in conjunction with the accompanying drawing.

DESCRIPTION OF THE PREFFERED EMBODIMENT

Figure 1:
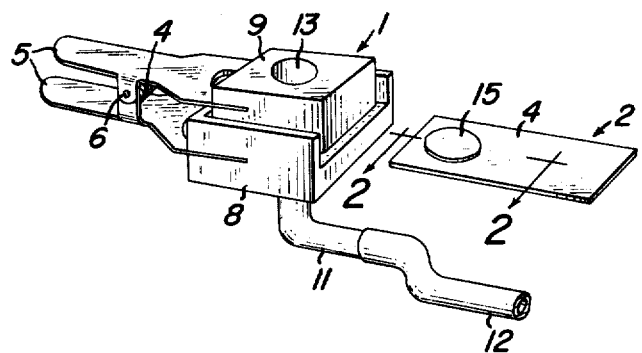
FIG. 1 shows the Robertson apparatus for collecting contaminants and the novel filter of my invention.

Referring to FIG. 1, numeral 1 is the Robertson sampling apparatus of U.S. Pat. No. 3,628,915 used in the present invention process and is shown as receiving the novel unitary filter and chromatography strip 2 of my invention.

Sampling apparatus 1, of FIG. 1, though not a part of the instant invention, is used therefor and is accordingly described; other samplers could be used as well. Apertured blocks 8 and 9 of brass are used to clamp filter 2 therebetween. Blocks 8 and 9 are hinged at pin 6 by way of arms 5 and held in compression by spring 4 with the free ends of arms 5 outermost. On the inner face of each block is secured a sealing ring, not shown. Aperture 13 extends through block 9. Tube 11 encloses the complementary aperture in block 8, so that a through passage exists from the upper face of block 9 through aperture 13, through its complement in block 8, on through to tube 11. The passage extends further; i.e., through rubber connecting tube 12 on to the pump means, not shown.

Figure 2:
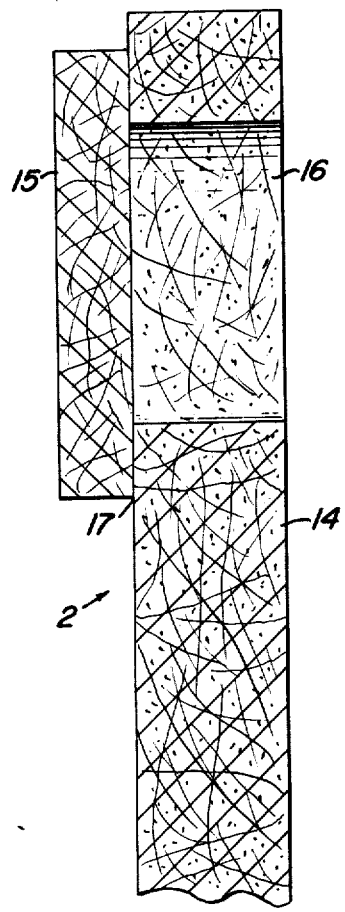
FIG. 2 shows the unitary filter of the invention of FIG. 1 depicted in cross-section.

My novel unitary sampling and analysis strip 2 is depicted in FIGS. 1 and 2. It comprises a support material 14 and filter 15. Filter 15 is secured to 14 as by any adhesive material 17, which will not have a deleterious affect upon the testing. "Sanfords' Grippit" glue works satisfactorily. Support material 14 may be in the form of a sheet or strip which has chromatrograhic adsorbent material therein. So also, it must have an area not covered with adsorbent material; i.e., an aperture 16 or removed area for the filter portion 15.

It is critical that chromatography adsorbent material not be present at or in the filter collecting area otherwise my novel process, to be explained later, will be inoperative. Relative proportions or sizes of materials are not critical, though there must be enough chromatographic adsorbent material extending in a continuous manner from the filter to enable chromatrograhpic spacing or separation results to be realized. A minimum of sixty millimeters seems to be adequate. Also, the filter area 15 on my unitary sampling and analysis strip must be located so that it accommodates, or is compatible with, the detection apparatus apertures. Hence, if for example the Robertson apparatus 1 of FIG. 1 be used, the filter area 15 must at least accommodate that of the aperture 13 and be located or extended back from the end of my novel unitary sampling and analysis strip.

Suitable support materials 14 are Gelman ITLC-SA or ITLS-SG strips made by Gelman Co. of Ann Arbor, Michigan. They are essentially made of a thin sheet stock or fiber material such as glass fiber and impregnated with conventional adsorbents such as silica gel of silicic acid. Though it is understood that other commercially available chromatography strip materials will also be adequate. Also, other well-known adsorbents will work as well.

Suitable filter material 15 can be of glass fiber, for example, or the like. It is critical that filter material 15 have sufficient porosity and permeability to enable gas or liquid flow therethrough while contemporaneously being relatively closed to collect the above mentioned contaminants. The permeability of the filter material and type will of course be dictated by the sample one desires to collect. Other equivalent materials will occur to one skilled in the art.

In the practice of my novel process with the use of my novel unitary sampling and analysis strip, I prefer to use the Robertson apparatus depicted in FIG. 1 and assigned to the instant assignee. It is understood, of course, that other apparatus would and could work. The only real need for the apparatus is to aid one in collecting the sample. In some cases, as for example where the fluid medium is more dense like a liquid, relative movement between the fluid to be tested and the filter is all that would be necessary.

Briefly, my novel process involves providing my unitary strip 2, depicted in FIGS. 1 and 2, with filter 15 and adsorbent 14. Then I collect a sample of contaminant on filter portion 15. This is done by engaging arms 5 of detector 1 and forcing the ends together to open blocks 8 and 9 readying them to receive my unitary strip 2. My unitary strip 2, with the filter portion 15 foremost, is inserted into detector 1 between blocks 8 and 9. Care must be used to assure that the filter overlays the block apertures 13. Then to ready my novel unitary strip 2 for sample collection, I release arms 5, thereby leaving strip 2 sealingly (by way of O-rings not shown) clamped (by way of spring 4) between blocks 8 and 9. Collecting the sample on the filter 15 is achieved by actuating the pump means, not shown, and causing the fluid to be sampled to flow through filter 15. Pump means can be any facility which creates a differential pressure so that fluid (gas, liquid, etc.) containing possible contaminants can be passed through the filter 15 to leave the contaminants deposited thereon. The route the fluid takes is through aperture 13, through filter 15, through the aperture in block 8 then through tubes 11 and 12 on to the pump means. After removing my unitary strip 2 from detector 1, I analyze the collected sample. One method is visually, either with or without amplification and/or light detector means such as ultraviolet light, to inspect the sample to determine the presence or lack of certain contaminants. Chromogenic reagents, fluorescence and conventional illuminators may be used to aid in accomplishing that end. So also, color chart comparisons can be made.

If the sample contains masking materials, as aforementioned, I first perform a chromatographic separation on the unitary strip and then inspect and analyze it for the presence of contaminants in the fashion above mentioned. This is accomplished by, for example, inserting my novel unitary strip 2, filter end first, into a vessel having one of the conventional chromatographic solvents in te bottom thereof. The depth of the solvent in the vessel should be about 5mm. The solvent rises up my unitary strip 2 via capillary action thereby creating the desired contaminant separation. After the separation step, I inspect the sample for contaminants. Now that the deleterious above mentioned masking materials have been displaced relative to the sought after contaminants my analysis is reliable.

The following examples further illustrate the use of my novel unitary strip in my novel contaminant detection and analysis process and should not be constructed to limit my invention in any way.

EXAMPLE 1

For the detection of glycolate agents the following procedure is used.

A unitary sampling and analysis strip is first constructed. Preferably, it should measure approximately 1 inches wide by 3 to 4 inches long. Gelman Co. provides silicic acid impregnated (ITLC-SA) chromatography sheet stock which works well for this purpose. Near one end thereof a portion is removed for the reception of the filter material. In this instance a 6 millimeter diameter hole is formed in any conventional manner. A filter is cut to overlay the hole. Suitable stock for this purpose can be had from the Gelman Company under the description of "glass microfiber" and from the Reeves Angel Company of Clifton, New Jersey, under their product designation of 934AH. The filter need only be large enough to provide bonding area around the periphery of the hole. The filter, once cut to size, is then bonded to the chromatography sheet stock with commercially available rubber cement. "Sansford's Grippit" glue works satisfactorily, however, any rubber or polymer base cement would work as well. After hardening, the unitary sampling and analysis strip is ready for use.

A sample is collected upon the strip by first inserting the unitary strip, filter portion first, into Robertson's apparatus in the fashion outlined above. The pump means is actuated and the fluid being tested is drawn through the filter for a suitable sampling period. The particle sizes of the contaminants, smokes, dyes, etc. of the fluid being detected are larger than the interstices defined by the filter fibers, therefore, anything on the filter is the sample. After removing the unitary strip from the detector apparatus, the sample on the filter portion is ready to be analyzed for glycolates.

Analysis encompasses, separation by chromatography, and final inspection and comparison for glycolates with the use of a reagent and ultra-violet light. To a two inch diameter, four inches deep, flat bottom, glass vessel is added a solvent methanol so that it is at a depth of about 5mm. Next, the sample containing unitary strip, filter end first is inserted into the vessel and into the solvent and the glass vessel is capped. Adsorption and capillary action must take place to get separation. Hence, this phenomena will commence upon solvent contact and should be allowed, for best separation, to continue until it travels at least 60 millimeters. After separation the unitary strip is left to dry at room temperature or oven heated to drive off the solvent. Once dry, the unitary strip is sprayed with a reagent to induce a fluorescent response with the glycolate agents. A reagent found to perform well in this capacity is 2-diphenylacetyl-1,3-indandione:1-p-dimethylaminobenzaldazine, the subject of patent application Ser. No. 851,142 filed Aug. 7, 1969, and now U.S. Pat. No. 3,956,281 and assigned to the instant assignee. After a few seconds, the unitary strip is inspected for the presence of the glycolate agents by the use of a long-wave ultra-violet light (366 nm). A yellow-orange color about halfway up the unitary strip indicates a positive test.

EXAMPLE 2

The procedure of Example 1 is again repeated except a Gelman's Company ITLS-SG sheet stock has been used for the chromatographic support. Results were reliable.

EXAMPLES 3–4

The procedure of Example 1 wherein acetone and chloroform were used as solvents. The results were reliable.

EXAMPLES 5–6

The procedure of Example 2 wherein acetone ahd chloroform were used as solvents. The results were reliable.

My unitary sampling and analysis strip can be used in any contaminant or specimen detecting process per se, however, because it also serves as a means for chromatography its utility and benefit is tenfold.

In summary, I wish it understood that I do not desire to be limited to the exact details of construction shown and described. It is understood, numerous chromogenic systems process, not named herein, are available to the artisan, and solvents, not named herein, are available to the artisan, numerous filters not named herein are available to artisan, and numerous chromatographic supports with diverse adsorbents not named herein are available to the artisan to practice my invention without departing therefrom.

I claim:

1. A method of detecting contaminants in fluids comprising the steps of: providing a unitary contaminant sampling and chromatographic analysis strip having a filter portion which is fluid porous with pores smaller than contaminants and a chromatographic portion disposed longitudinally therefrom: collecting a contaminant sample upon the said filter portion by traversely passing a contaminant containing fluid through the pores of the filter portion without engaging the said chromatographic portion and thereby leaving a contaminant sample upon said filter portion; chromatographing said sample with the application of a solvent to the sample and said strip; and then analyzing the resultant chromatographic portion.

* * * * *